United States Patent
Elliott (10) Patent No.: US 7,311,658 B2
(45) Date of Patent: Dec. 25, 2007

(54) METHOD AND SYSTEM PROVIDING A FUNDAMENTAL MUSICAL INTERVAL FOR HEART RATE VARIABILITY SYNCHRONIZATION

(75) Inventor: Stephen Bennett Elliott, Allen, TX (US)

(73) Assignee: Coherence LLC, Allen, TX (US)

( * ) Notice: Subject to any disclaimer, the term of this patent is extended or adjusted under 35 U.S.C. 154(b) by 685 days.

(21) Appl. No.: 10/808,482

(22) Filed: Mar. 25, 2004

(65) Prior Publication Data

US 2005/0215846 A1    Sep. 29, 2005

(51) Int. Cl.
*A61M 21/02*    (2006.01)
(52) U.S. Cl. .................... 600/28; 600/484; 128/905; 84/652
(58) Field of Classification Search ................ 600/28, 600/26, 483, 484, 559, 529; 128/905; 434/262, 434/265; 84/652
See application file for complete search history.

(56) References Cited

U.S. PATENT DOCUMENTS

| | | | |
|---|---|---|---|
| 5,076,281 A * | 12/1991 | Gavish | 600/534 |
| 2004/0116784 A1* | 6/2004 | Gavish | 600/300 |
| 2004/0225340 A1* | 11/2004 | Evans | 607/88 |

* cited by examiner

*Primary Examiner*—Kennedy J. Schaetzle
(74) *Attorney, Agent, or Firm*—Withrow & Terranova, PLLC (57) ABSTRACT

A broad method consisting of the composition and creation of music wherein musical cues are contained for the purpose of synchronizing the breathing cycle with a 5.88 second musical interval for the purpose of synchronizing the heart rate variability cycle with the breathing cycle. The method wherein a 5.88 second interval is incorporated into musical composition for the purpose of producing said music and the identification and incorporation of 21 novel tempos as the basis of producing said interval. Also addressed is the method and system of incorporating the 21 novel tempos into metronomes and music synthesizers for the purpose of producing said tempos and music of said tempos, respectively.

43 Claims, 9 Drawing Sheets

100
Musical Tempo According to Present State of the Art As Defined by Maelzel's Metronome

| 102 | 103 | 104 |
|---|---|---|
| Beats/ 60 Seconds | Interval (Seconds) | Beats/ Second |
| 1.0000 | 60.0000 | 0.0167 |
| 2.0000 | 30.0000 | 0.0333 |
| 3.0000 | 20.0000 | 0.0500 |
| 4.0000 | 15.0000 | 0.0667 |
| 5.0000 | 12.0000 | 0.0833 |
| 6.0000 | 10.0000 | 0.1000 |
| 7.0000 | 8.5714 | 0.1167 |
| 8.0000 | 7.5000 | 0.1333 |
| 9.0000 | 6.6667 | 0.1500 |
| 10.0000 | 6.0000 | 0.1667 |
| 11.0000 | 5.4545 | 0.1833 |
| 12.0000 | 5.0000 | 0.2000 |
| 13.0000 | 4.6154 | 0.2167 |
| 14.0000 | 4.2857 | 0.2333 |
| 15.0000 | 4.0000 | 0.2500 |
| 16.0000 | 3.7500 | 0.2667 |
| 17.0000 | 3.5294 | 0.2833 |
| 18.0000 | 3.3333 | 0.3000 |
| 19.0000 | 3.1579 | 0.3167 |
| 20.0000 | 3.0000 | 0.3333 |
| 21.0000 | 2.8571 | 0.3500 |
| 22.0000 | 2.7273 | 0.3667 |
| 23.0000 | 2.6087 | 0.3833 |
| 24.0000 | 2.5000 | 0.4000 |
| 25.0000 | 2.4000 | 0.4167 |
| 26.0000 | 2.3077 | 0.4333 |
| 27.0000 | 2.2222 | 0.4500 |
| 28.0000 | 2.1429 | 0.4667 |
| 29.0000 | 2.0690 | 0.4833 |
| 30.0000 | 2.0000 | 0.5000 |
| 31.0000 | 1.9355 | 0.5167 |
| 32.0000 | 1.8750 | 0.5333 |
| 33.0000 | 1.8182 | 0.5500 |
| 34.0000 | 1.7647 | 0.5667 |
| 35.0000 | 1.7143 | 0.5833 |
| 36.0000 | 1.6667 | 0.6000 |
| 37.0000 | 1.6216 | 0.6167 |
| 38.0000 | 1.5789 | 0.6333 |
| 39.0000 | 1.5385 | 0.6500 |
| 40.0000 | 1.5000 | 0.6667 |
| 41.0000 | 1.4634 | 0.6833 |
| 42.0000 | 1.4286 | 0.7000 |
| 43.0000 | 1.3953 | 0.7167 |
| 44.0000 | 1.3636 | 0.7333 |
| 45.0000 | 1.3333 | 0.7500 |
| 46.0000 | 1.3043 | 0.7667 |
| 47.0000 | 1.2766 | 0.7833 |
| 48.0000 | 1.2500 | 0.8000 |
| 49.0000 | 1.2245 | 0.8167 |
| 50.0000 | 1.2000 | 0.8333 |
| 51.0000 | 1.1765 | 0.8500 |
| 52.0000 | 1.1538 | 0.8667 |
| 53.0000 | 1.1321 | 0.8833 |

107
Musical Tempo as Defined by the Preferred Embodiment of the Present Invention

| | 108 | 109 | 110 | 111 |
|---|---|---|---|---|
| | Beats/60 Seconds | Interval (Seconds) | Beats/ Second | 5.88 Sec Divided by Interval |
| | 1.0000 | 60.0000 | 0.0167 | 0.0980 |
| | 2.0000 | 30.0000 | 0.0333 | 0.1961 |
| | 3.0000 | 20.0000 | 0.0500 | 0.2941 |
| | 4.0000 | 15.0000 | 0.0667 | 0.3922 |
| | 5.0000 | 12.0000 | 0.0833 | 0.4902 |
| | 6.0000 | 10.0000 | 0.1000 | 0.5882 |
| | 7.0000 | 8.5714 | 0.1167 | 0.6863 |
| | 8.0000 | 7.5000 | 0.1333 | 0.7843 |
| | 9.0000 | 6.6667 | 0.1500 | 0.8824 |
| | 10.0000 | 6.0000 | 0.1667 | 0.9804 |
| | 10.2000 | 5.8824 | 0.1700 | 1.0000 |
| | 11.0000 | 5.4545 | 0.1833 | 1.0784 |
| | 12.0000 | 5.0000 | 0.2000 | 1.1765 |
| | 13.0000 | 4.6154 | 0.2167 | 1.2745 |
| | 14.0000 | 4.2857 | 0.2333 | 1.3726 |
| | 15.0000 | 4.0000 | 0.2500 | 1.4706 |
| | 16.0000 | 3.7500 | 0.2667 | 1.5686 |
| | 17.0000 | 3.5294 | 0.2833 | 1.6667 |
| | 18.0000 | 3.3333 | 0.3000 | 1.7647 |
| | 19.0000 | 3.1579 | 0.3167 | 1.8628 |
| | 20.0000 | 3.0000 | 0.3333 | 1.9608 |
| 113 | 20.4000 | 2.9412 | 0.3400 | 2.0000 |
| | 21.0000 | 2.8571 | 0.3500 | 2.0588 |
| | 22.0000 | 2.7273 | 0.3667 | 2.1569 |
| | 23.0000 | 2.6087 | 0.3833 | 2.2549 |
| | 24.0000 | 2.5000 | 0.4000 | 2.3530 |
| | 25.0000 | 2.4000 | 0.4167 | 2.4510 |
| | 26.0000 | 2.3077 | 0.4333 | 2.5490 |
| | 27.0000 | 2.2222 | 0.4500 | 2.6471 |
| | 28.0000 | 2.1429 | 0.4667 | 2.7451 |
| | 29.0000 | 2.0690 | 0.4833 | 2.8432 |
| | 30.0000 | 2.0000 | 0.5000 | 2.9412 |
| 114 | 30.6000 | 1.9608 | 0.5100 | 3.0000 |
| | 31.0000 | 1.9355 | 0.5167 | 3.0392 |
| | 32.0000 | 1.8750 | 0.5333 | 3.1373 |
| | 33.0000 | 1.8182 | 0.5500 | 3.2353 |
| | 34.0000 | 1.7647 | 0.5667 | 3.3334 |
| | 35.0000 | 1.7143 | 0.5833 | 3.4314 |
| | 36.0000 | 1.6667 | 0.6000 | 3.5294 |
| | 37.0000 | 1.6216 | 0.6167 | 3.6275 |
| | 38.0000 | 1.5789 | 0.6333 | 3.7255 |
| | 39.0000 | 1.5385 | 0.6500 | 3.8236 |
| | 40.0000 | 1.5000 | 0.6667 | 3.9216 |
| 115 | 40.8000 | 1.4706 | 0.6800 | 4.0000 |
| | 41.0000 | 1.4634 | 0.6833 | 4.0196 |
| | 42.0000 | 1.4286 | 0.7000 | 4.1177 |
| | 43.0000 | 1.3953 | 0.7167 | 4.2157 |
| | 44.0000 | 1.3636 | 0.7333 | 4.3138 |
| | 45.0000 | 1.3333 | 0.7500 | 4.4118 |
| | 46.0000 | 1.3043 | 0.7667 | 4.5098 |
| | 47.0000 | 1.2766 | 0.7833 | 4.6079 |
| | 48.0000 | 1.2500 | 0.8000 | 4.7059 |
| | 49.0000 | 1.2245 | 0.8167 | 4.8040 |
| | 50.0000 | 1.2000 | 0.8333 | 4.9020 |
| 116 | 51.0000 | 1.1765 | 0.8500 | 5.0000 |
| | 52.0000 | 1.1538 | 0.8667 | 5.0981 |
| | 53.0000 | 1.1321 | 0.8833 | 5.1961 |

FIGURE 1

| | | | | | | | |
|---|---|---|---|---|---|---|---|
| 54.0000 | 1.1111 | 0.9000 | | | 54.0000 | 1.1111 | 0.9000 | 5.2942 |
| 55.0000 | 1.0909 | 0.9167 | | | 55.0000 | 1.0909 | 0.9167 | 5.3922 |
| 56.0000 | 1.0714 | 0.9333 | | | 56.0000 | 1.0714 | 0.9333 | 5.4902 |
| 57.0000 | 1.0526 | 0.9500 | | | 57.0000 | 1.0526 | 0.9500 | 5.5883 |
| 58.0000 | 1.0345 | 0.9667 | | | 58.0000 | 1.0345 | 0.9667 | 5.6863 |
| 59.0000 | 1.0169 | 0.9833 | | | 59.0000 | 1.0169 | 0.9833 | 5.7844 |
| 60.0000 | 1.0000 | 1.0000 | | | 60.0000 | 1.0000 | 1.0000 | 5.8824 |
| 61.0000 | 0.9836 | 1.0167 | | | 61.0000 | 0.9836 | 1.0167 | 5.9804 |
| | | | | 117 | 61.2000 | 0.9804 | 1.0200 | 6.0000 |
| 62.0000 | 0.9677 | 1.0333 | | | 62.0000 | 0.9677 | 1.0333 | 6.0785 |
| 63.0000 | 0.9524 | 1.0500 | | | 63.0000 | 0.9524 | 1.0500 | 6.1765 |
| 64.0000 | 0.9375 | 1.0667 | | | 64.0000 | 0.9375 | 1.0667 | 6.2746 |
| 65.0000 | 0.9231 | 1.0833 | | | 65.0000 | 0.9231 | 1.0833 | 6.3726 |
| 66.0000 | 0.9091 | 1.1000 | | | 66.0000 | 0.9091 | 1.1000 | 6.4706 |
| 67.0000 | 0.8955 | 1.1167 | | | 67.0000 | 0.8955 | 1.1167 | 6.5687 |
| 68.0000 | 0.8824 | 1.1333 | | | 68.0000 | 0.8824 | 1.1333 | 6.6667 |
| 69.0000 | 0.8696 | 1.1500 | | | 69.0000 | 0.8696 | 1.1500 | 6.7648 |
| 70.0000 | 0.8571 | 1.1667 | | | 70.0000 | 0.8571 | 1.1667 | 6.8628 |
| 71.0000 | 0.8451 | 1.1833 | | | 71.0000 | 0.8451 | 1.1833 | 6.9608 |
| | | | | 118 | 71.4000 | 0.8403 | 1.1900 | 7.0001 |
| 72.0000 | 0.8333 | 1.2000 | | | 72.0000 | 0.8333 | 1.2000 | 7.0589 |
| 73.0000 | 0.8219 | 1.2167 | | | 73.0000 | 0.8219 | 1.2167 | 7.1569 |
| 74.0000 | 0.8108 | 1.2333 | | | 74.0000 | 0.8108 | 1.2333 | 7.2550 |
| 75.0000 | 0.8000 | 1.2500 | | | 75.0000 | 0.8000 | 1.2500 | 7.3530 |
| 76.0000 | 0.7895 | 1.2667 | | | 76.0000 | 0.7895 | 1.2667 | 7.4510 |
| 77.0000 | 0.7792 | 1.2833 | | | 77.0000 | 0.7792 | 1.2833 | 7.5491 |
| 78.0000 | 0.7692 | 1.3000 | | | 78.0000 | 0.7692 | 1.3000 | 7.6471 |
| 79.0000 | 0.7595 | 1.3167 | | | 79.0000 | 0.7595 | 1.3167 | 7.7452 |
| 80.0000 | 0.7500 | 1.3333 | | | 80.0000 | 0.7500 | 1.3333 | 7.8432 |
| 81.0000 | 0.7407 | 1.3500 | | | 81.0000 | 0.7407 | 1.3500 | 7.9412 |
| | | | | 119 | 81.6000 | 0.7353 | 1.3600 | 8.0001 |
| 82.0000 | 0.7317 | 1.3667 | | | 82.0000 | 0.7317 | 1.3667 | 8.0393 |
| 83.0000 | 0.7229 | 1.3833 | | | 83.0000 | 0.7229 | 1.3833 | 8.1373 |
| 84.0000 | 0.7143 | 1.4000 | | | 84.0000 | 0.7143 | 1.4000 | 8.2354 |
| 85.0000 | 0.7059 | 1.4167 | | | 85.0000 | 0.7059 | 1.4167 | 8.3334 |
| 86.0000 | 0.6977 | 1.4333 | | | 86.0000 | 0.6977 | 1.4333 | 8.4314 |
| 87.0000 | 0.6897 | 1.4500 | | | 87.0000 | 0.6897 | 1.4500 | 8.5295 |
| 88.0000 | 0.6818 | 1.4667 | | | 88.0000 | 0.6818 | 1.4667 | 8.6275 |
| 89.0000 | 0.6742 | 1.4833 | | | 89.0000 | 0.6742 | 1.4833 | 8.7256 |
| 90.0000 | 0.6667 | 1.5000 | | | 90.0000 | 0.6667 | 1.5000 | 8.8236 |
| 91.0000 | 0.6593 | 1.5167 | | | 91.0000 | 0.6593 | 1.5167 | 8.9216 |
| | | | | 120 | 91.8000 | 0.6536 | 1.5300 | 9.0001 |
| 92.0000 | 0.6522 | 1.5333 | | | 92.0000 | 0.6522 | 1.5333 | 9.0197 |
| 93.0000 | 0.6452 | 1.5500 | | | 93.0000 | 0.6452 | 1.5500 | 9.1177 |
| 94.0000 | 0.6383 | 1.5667 | | | 94.0000 | 0.6383 | 1.5667 | 9.2158 |
| 95.0000 | 0.6316 | 1.5833 | | | 95.0000 | 0.6316 | 1.5833 | 9.3138 |
| 96.0000 | 0.6250 | 1.6000 | | | 96.0000 | 0.6250 | 1.6000 | 9.4118 |
| 97.0000 | 0.6186 | 1.6167 | | | 97.0000 | 0.6186 | 1.6167 | 9.5099 |
| 98.0000 | 0.6122 | 1.6333 | | | 98.0000 | 0.6122 | 1.6333 | 9.6079 |
| 99.0000 | 0.6061 | 1.6500 | | | 99.0000 | 0.6061 | 1.6500 | 9.7060 |
| 100.0000 | 0.6000 | 1.6667 | | | 100.0000 | 0.6000 | 1.6667 | 9.8040 |
| 101.0000 | 0.5941 | 1.6833 | | | 101.0000 | 0.5941 | 1.6833 | 9.9020 |
| 102.0000 | 0.5882 | 1.7000 | | 121 | 102.0000 | 0.5882 | 1.7000 | 10.0001 |
| 103.0000 | 0.5825 | 1.7167 | | | 103.0000 | 0.5825 | 1.7167 | 10.0981 |
| 104.0000 | 0.5769 | 1.7333 | | | 104.0000 | 0.5769 | 1.7333 | 10.1962 |
| 105.0000 | 0.5714 | 1.7500 | | | 105.0000 | 0.5714 | 1.7500 | 10.2942 |
| 106.0000 | 0.5660 | 1.7667 | | | 106.0000 | 0.5660 | 1.7667 | 10.3922 |
| 107.0000 | 0.5607 | 1.7833 | | | 107.0000 | 0.5607 | 1.7833 | 10.4903 |
| 108.0000 | 0.5556 | 1.8000 | | | 108.0000 | 0.5556 | 1.8000 | 10.5883 |
| 109.0000 | 0.5505 | 1.8167 | | | 109.0000 | 0.5505 | 1.8167 | 10.6864 |
| 110.0000 | 0.5455 | 1.8333 | | | 110.0000 | 0.5455 | 1.8333 | 10.7844 |
| 111.0000 | 0.5405 | 1.8500 | | | 111.0000 | 0.5405 | 1.8500 | 10.8824 |
| 112.0000 | 0.5357 | 1.8667 | | | 112.0000 | 0.5357 | 1.8667 | 10.9805 |
| | | | | 122 | 112.2000 | 0.5348 | 1.8700 | 11.0001 |
| 113.0000 | 0.5310 | 1.8833 | | | 113.0000 | 0.5310 | 1.8833 | 11.0785 |
| 114.0000 | 0.5263 | 1.9000 | | | 114.0000 | 0.5263 | 1.9000 | 11.1766 |
| 115.0000 | 0.5217 | 1.9167 | | | 115.0000 | 0.5217 | 1.9167 | 11.2746 |

FIGURE 1 continued

| | | | | | | | |
|---|---|---|---|---|---|---|---|
| 116.0000 | 0.5172 | 1.9333 | | | 116.0000 | 0.5172 | 1.9333 | 11.3726 |
| 117.0000 | 0.5128 | 1.9500 | | | 117.0000 | 0.5128 | 1.9500 | 11.4707 |
| 118.0000 | 0.5085 | 1.9667 | | | 118.0000 | 0.5085 | 1.9667 | 11.5687 |
| 119.0000 | 0.5042 | 1.9833 | | | 119.0000 | 0.5042 | 1.9833 | 11.6668 |
| 120.0000 | 0.5000 | 2.0000 | | | 120.0000 | 0.5000 | 2.0000 | 11.7648 |
| 121.0000 | 0.4959 | 2.0167 | | | 121.0000 | 0.4959 | 2.0167 | 11.8828 |
| 122.0000 | 0.4918 | 2.0333 | | | 122.0000 | 0.4918 | 2.0333 | 11.9609 |
| | | | | 123 | 122.4000 | 0.4902 | 2.0400 | 12.0001 |
| 123.0000 | 0.4878 | 2.0500 | | | 123.0000 | 0.4878 | 2.0500 | 12.0589 |
| 124.0000 | 0.4839 | 2.0667 | | | 124.0000 | 0.4839 | 2.0667 | 12.1570 |
| 125.0000 | 0.4800 | 2.0833 | | | 125.0000 | 0.4800 | 2.0833 | 12.2550 |
| 126.0000 | 0.4762 | 2.1000 | | | 126.0000 | 0.4762 | 2.1000 | 12.3530 |
| 127.0000 | 0.4724 | 2.1167 | | | 127.0000 | 0.4724 | 2.1167 | 12.4511 |
| 128.0000 | 0.4688 | 2.1333 | | | 128.0000 | 0.4688 | 2.1333 | 12.5491 |
| 129.0000 | 0.4651 | 2.1500 | | | 129.0000 | 0.4651 | 2.1500 | 12.6472 |
| 130.0000 | 0.4615 | 2.1667 | | | 130.0000 | 0.4615 | 2.1667 | 12.7452 |
| 131.0000 | 0.4580 | 2.1833 | | | 131.0000 | 0.4580 | 2.1833 | 12.8432 |
| 132.0000 | 0.4545 | 2.2000 | | | 132.0000 | 0.4545 | 2.2000 | 12.9413 |
| | | | | 124 | 132.6000 | 0.4525 | 2.2100 | 13.0001 |
| 133.0000 | 0.4511 | 2.2167 | | | 133.0000 | 0.4511 | 2.2167 | 13.0393 |
| 134.0000 | 0.4478 | 2.2333 | | | 134.0000 | 0.4478 | 2.2333 | 13.1374 |
| 135.0000 | 0.4444 | 2.2500 | | | 135.0000 | 0.4444 | 2.2500 | 13.2354 |
| 136.0000 | 0.4412 | 2.2667 | | | 136.0000 | 0.4412 | 2.2667 | 13.3334 |
| 137.0000 | 0.4380 | 2.2833 | | | 137.0000 | 0.4380 | 2.2833 | 13.4315 |
| 138.0000 | 0.4348 | 2.3000 | | | 138.0000 | 0.4348 | 2.3000 | 13.5295 |
| 139.0000 | 0.4317 | 2.3167 | | | 139.0000 | 0.4317 | 2.3167 | 13.6276 |
| 140.0000 | 0.4286 | 2.3333 | | | 140.0000 | 0.4286 | 2.3333 | 13.7256 |
| 141.0000 | 0.4255 | 2.3500 | | | 141.0000 | 0.4255 | 2.3500 | 13.8236 |
| 142.0000 | 0.4225 | 2.3667 | | | 142.0000 | 0.4225 | 2.3667 | 13.9217 |
| | | | | 125 | 142.8000 | 0.4202 | 2.3800 | 14.0001 |
| 143.0000 | 0.4196 | 2.3833 | | | 143.0000 | 0.4196 | 2.3833 | 14.0197 |
| 144.0000 | 0.4167 | 2.4000 | | | 144.0000 | 0.4167 | 2.4000 | 14.1178 |
| 145.0000 | 0.4138 | 2.4167 | | | 145.0000 | 0.4138 | 2.4167 | 14.2158 |
| 146.0000 | 0.4110 | 2.4333 | | | 146.0000 | 0.4110 | 2.4333 | 14.3138 |
| 147.0000 | 0.4082 | 2.4500 | | | 147.0000 | 0.4082 | 2.4500 | 14.4119 |
| 148.0000 | 0.4054 | 2.4667 | | | 148.0000 | 0.4054 | 2.4667 | 14.5099 |
| 149.0000 | 0.4027 | 2.4833 | | | 149.0000 | 0.4027 | 2.4833 | 14.6080 |
| 150.0000 | 0.4000 | 2.5000 | | | 150.0000 | 0.4000 | 2.5000 | 14.7060 |
| 151.0000 | 0.3974 | 2.5167 | | | 151.0000 | 0.3974 | 2.5167 | 14.8040 |
| 152.0000 | 0.3947 | 2.5333 | | | 152.0000 | 0.3947 | 2.5333 | 14.9021 |
| 153.0000 | 0.3922 | 2.5500 | | 126 | 153.0000 | 0.3922 | 2.5500 | 15.0001 |
| 154.0000 | 0.3896 | 2.5667 | | | 154.0000 | 0.3896 | 2.5667 | 15.0982 |
| 155.0000 | 0.3871 | 2.5833 | | | 155.0000 | 0.3871 | 2.5833 | 15.1962 |
| 156.0000 | 0.3846 | 2.6000 | | | 156.0000 | 0.3846 | 2.6000 | 15.2942 |
| 157.0000 | 0.3822 | 2.6167 | | | 157.0000 | 0.3822 | 2.6167 | 15.3923 |
| 158.0000 | 0.3797 | 2.6333 | | | 158.0000 | 0.3797 | 2.6333 | 15.4903 |
| 159.0000 | 0.3774 | 2.6500 | | | 159.0000 | 0.3774 | 2.6500 | 15.5884 |
| 160.0000 | 0.3750 | 2.6667 | | | 160.0000 | 0.3750 | 2.6667 | 15.6864 |
| 161.0000 | 0.3727 | 2.6833 | | | 161.0000 | 0.3727 | 2.6833 | 15.7844 |
| 162.0000 | 0.3704 | 2.7000 | | | 162.0000 | 0.3704 | 2.7000 | 15.8825 |
| 163.0000 | 0.3681 | 2.7167 | | | 163.0000 | 0.3681 | 2.7167 | 15.9805 |
| | | | | 127 | 163.2000 | 0.3676 | 2.7200 | 16.0001 |
| 164.0000 | 0.3659 | 2.7333 | | | 164.0000 | 0.3659 | 2.7333 | 16.0786 |
| 165.0000 | 0.3636 | 2.7500 | | | 165.0000 | 0.3636 | 2.7500 | 16.1766 |
| 166.0000 | 0.3614 | 2.7667 | | | 166.0000 | 0.3614 | 2.7667 | 16.2746 |
| 167.0000 | 0.3593 | 2.7833 | | | 167.0000 | 0.3593 | 2.7833 | 16.3727 |
| 168.0000 | 0.3571 | 2.8000 | | | 168.0000 | 0.3571 | 2.8000 | 16.4707 |
| 169.0000 | 0.3550 | 2.8167 | | | 169.0000 | 0.3550 | 2.8167 | 16.5688 |
| 170.0000 | 0.3529 | 2.8333 | | | 170.0000 | 0.3529 | 2.8333 | 16.6668 |
| 171.0000 | 0.3509 | 2.8500 | | | 171.0000 | 0.3509 | 2.8500 | 16.7648 |
| 172.0000 | 0.3488 | 2.8667 | | | 172.0000 | 0.3488 | 2.8667 | 16.8829 |
| 173.0000 | 0.3468 | 2.8833 | | | 173.0000 | 0.3468 | 2.8833 | 16.9609 |
| | | | | 128 | 173.4000 | 0.3460 | 2.8900 | 17.0001 |
| 174.0000 | 0.3448 | 2.9000 | | | 174.0000 | 0.3448 | 2.9000 | 17.0590 |
| 175.0000 | 0.3429 | 2.9167 | | | 175.0000 | 0.3429 | 2.9167 | 17.1570 |
| 176.0000 | 0.3409 | 2.9333 | | | 176.0000 | 0.3409 | 2.9333 | 17.2550 |
| 177.0000 | 0.3390 | 2.9500 | | | 177.0000 | 0.3390 | 2.9500 | 17.3531 |

FIGURE 1 continued

| | | | | | | | |
|---|---|---|---|---|---|---|---|
| | 178.0000 | 0.3371 | 2.9667 | | 178.0000 | 0.3371 | 2.9667 | 17.4511 |
| | 179.0000 | 0.3352 | 2.9833 | | 179.0000 | 0.3352 | 2.9833 | 17.5492 |
| | 180.0000 | 0.3333 | 3.0000 | | 180.0000 | 0.3333 | 3.0000 | 17.6472 |
| | 181.0000 | 0.3315 | 3.0167 | | 181.0000 | 0.3315 | 3.0167 | 17.7452 |
| | 182.0000 | 0.3297 | 3.0333 | | 182.0000 | 0.3297 | 3.0333 | 17.8433 |
| | 183.0000 | 0.3279 | 3.0500 | | 183.0000 | 0.3279 | 3.0500 | 17.9413 |
| | | | | 129 | 183.6000 | 0.3268 | 3.0600 | 18.0001 |
| | 184.0000 | 0.3261 | 3.0667 | | 184.0000 | 0.3261 | 3.0667 | 18.0394 |
| | 185.0000 | 0.3243 | 3.0833 | | 185.0000 | 0.3243 | 3.0833 | 18.1374 |
| | 186.0000 | 0.3226 | 3.1000 | | 186.0000 | 0.3226 | 3.1000 | 18.2354 |
| | 187.0000 | 0.3209 | 3.1167 | | 187.0000 | 0.3209 | 3.1167 | 18.3335 |
| | 188.0000 | 0.3191 | 3.1333 | | 188.0000 | 0.3191 | 3.1333 | 18.4315 |
| | 189.0000 | 0.3175 | 3.1500 | | 189.0000 | 0.3175 | 3.1500 | 18.5296 |
| | 190.0000 | 0.3158 | 3.1667 | | 190.0000 | 0.3158 | 3.1667 | 18.6276 |
| | 191.0000 | 0.3141 | 3.1833 | | 191.0000 | 0.3141 | 3.1833 | 18.7256 |
| | 192.0000 | 0.3125 | 3.2000 | | 192.0000 | 0.3125 | 3.2000 | 18.8237 |
| | 193.0000 | 0.3109 | 3.2167 | | 193.0000 | 0.3109 | 3.2167 | 18.9217 |
| | | | | 130 | 193.8000 | 0.3096 | 3.2300 | 19.0002 |
| | 194.0000 | 0.3093 | 3.2333 | | 194.0000 | 0.3093 | 3.2333 | 19.0198 |
| | 195.0000 | 0.3077 | 3.2500 | | 195.0000 | 0.3077 | 3.2500 | 19.1178 |
| | 196.0000 | 0.3061 | 3.2667 | | 196.0000 | 0.3061 | 3.2667 | 19.2158 |
| | 197.0000 | 0.3046 | 3.2833 | | 197.0000 | 0.3046 | 3.2833 | 19.3139 |
| | 198.0000 | 0.3030 | 3.3000 | | 198.0000 | 0.3030 | 3.3000 | 19.4119 |
| | 199.0000 | 0.3015 | 3.3167 | | 199.0000 | 0.3015 | 3.3167 | 19.5100 |
| | 200.0000 | 0.3000 | 3.3333 | | 200.0000 | 0.3000 | 3.3333 | 19.6080 |
| | 201.0000 | 0.2985 | 3.3500 | | 201.0000 | 0.2985 | 3.3500 | 19.7060 |
| | 202.0000 | 0.2970 | 3.3667 | | 202.0000 | 0.2970 | 3.3667 | 19.8041 |
| | 203.0000 | 0.2956 | 3.3833 | | 203.0000 | 0.2956 | 3.3833 | 19.9021 |
| | 204.0000 | 0.2941 | 3.4000 | 131 | 204.0000 | 0.2941 | 3.4000 | 20.0002 |
| | 205.0000 | 0.2927 | 3.4167 | | 205.0000 | 0.2927 | 3.4167 | 20.0982 |
| | 206.0000 | 0.2913 | 3.4333 | | 206.0000 | 0.2913 | 3.4333 | 20.1962 |
| | 207.0000 | 0.2899 | 3.4500 | | 207.0000 | 0.2899 | 3.4500 | 20.2943 |
| 106 | 208.0000 | 0.2885 | 3.4667 | | 208.0000 | 0.2885 | 3.4667 | 20.3923 |
| | 209.0000 | 0.2871 | 3.4833 | | 209.0000 | 0.2871 | 3.4833 | 20.4904 |
| | 210.0000 | 0.2857 | 3.5000 | | 210.0000 | 0.2857 | 3.5000 | 20.5884 |
| | 211.0000 | 0.2844 | 3.5167 | | 211.0000 | 0.2844 | 3.5167 | 20.6864 |
| | 212.0000 | 0.2830 | 3.5333 | | 212.0000 | 0.2830 | 3.5333 | 20.7845 |
| | 213.0000 | 0.2817 | 3.5500 | | 213.0000 | 0.2817 | 3.5500 | 20.8825 |
| | 214.0000 | 0.2804 | 3.5667 | | 214.0000 | 0.2804 | 3.5667 | 20.9806 |
| | | | | 132 | 214.2000 | 0.2801 | 3.5700 | 21.0002 |

METHOD AND SYSTEM PROVIDING A FUNDAMENTAL MUSICAL INTERVAL FOR HEART RATE VARIABILITY SYNCHRONIZATION

RELATED PATENT FILINGS

Method and System for Conciously Synchronizing the Breathing Cycle with the Natural Heart Rate Cycle (Ser. No. 10/699,025), Method and System for Synchronizing the Heart Rate Variability Cycle With The Breathing Cycle (Feb. 19, 2004), Method of Presenting Audible and Visual Cues for Synchronizing the Breathing Cycle With An External Timing Reference for Purposes of Synchronizing The Heart Rate Variability Cycle With The Breathing Cycle (Mar. 15, 2004)

FIELD OF THE INVENTION

The present invention relates to the field of human physiology, and in particular to a method and system for allowing a human subject to consciously control physiological processes, more particularly, it allows a human subject to achieve synchronization of the natural heart rate variability cycle with the breathing cycle via conscious synchronization of the breathing cycle with an audible timing reference, and more particularly to the creation of a musical standard by which the audible timing reference may be incorporated into musical composition.

BACKGROUND OF THE INVENTION

The human heart is known to have its own nervous system and its own natural tendency toward rhythm. For purposes of this invention, there are two primary aspects to this rhythm, the heartbeat rate, and the rate at which the heartbeat rate changes otherwise known as heart rate variability. Heartbeat rate is usually specified in absolute number of heartbeats occurring during a specified period. Heartbeat rate variability, otherwise know as heart rate variability is the change in heartbeat rate as occurs during a specified period. Henceforth, heartbeat rate variability will be referred to as heart rate variability.

While the heart has its own tendency toward rhythm, it is closely coupled to breathing. The relationship is such that as inhalation occurs, the heartbeat rate tends to increase and as exhalation occurs, the heartbeat rate tends to decrease. It is important to note that while the heartbeat rate and breathing rate influence each other, the relationship is a plesiochronous one, that is, they are independent rhythms that strongly influence but do not directly control each other.

It is generally recognized that heart rate variability is an indicator of physiological and emotional state, that is, irregular incoherent heart rate variability indicates a condition of physiological/psychological stress. Alternatively, a highly regular coherent heart rate variability is indicative of a condition of physiological/psychological harmony.

Accordingly, it is highly desirable to achieve and maintain a highly coherent heart rate variability as life circumstances permit. This having been said, with proper training and the application of the present invention, it is possible for a human subject to rapidly achieve the desired state of high coherence of heart rate variability and to reinforce that coherence on an ongoing basis.

The present invention takes advantage of the relationship between the breathing cycle and the natural heart rate variability cycle to bring heart rate variability to the desired state of coherence and the human subject to the resultant state of physiological and emotional harmony. It accomplishes this via synchronization of the heart rate variability cycle with the breathing cycle. More specifically, it accomplishes this by integrating audible cues in the form of recurring identifiable musical sequences with a fundamental periodicity of 5.88 seconds into musical composition. When a musical composition according to the preferred embodiment of the present invention is played, the listener(s) or singer(s) consciously synchronizes their breathing cycle to the recurring musical pattern, thereby synchronizing their heart rate variability cycle with their breathing cycle.

SUMMARY OF THE INVENTION

As previously described, a relationship exists between the heartbeat rate specified in terms of heart rate variability, and the breathing cycle. While the heart has its own tendency toward a natural variable rhythm, there is a strong correlation with breathing according to this specific relationship: as inhalation occurs, there is a tendency for the heartbeat rate to increase, as exhalation occurs, there is a tendency for the heartbeat rate to decrease. In a relaxed or semi-active human subject, the effect of the breathing cycle on the heart rate variability cycle is extremely strong. In fact, the heart rate variability cycle will synchronize with the breathing cycle if the breathing cycle is highly attuned to the periodicity of the natural heart rate variability cycle. The nominal period of the typical human heart rate variability cycle is 11.76 seconds. Therefore, if the period of the breathing cycle is timed to 11.76 seconds, the heart rate variability cycle will synchronize with it, bringing the natural heart rate variability cycle into phase synchrony with the breathing cycle and thereby bringing the subject's heart rate variability cycle into the desired state of coherence.

The present invention accomplishes this by presenting the human subject with musical cues to which the breathing cycle is consciously synchronized. These musical cues are identifiable recurring sequences with a fundamental periodicity of 11.76 seconds divided by 2, or 5.88 seconds, representing the 50% of the 11.76 second heart rate variability cycle and corresponding to 50% of the breathing cycle of like period, that is, the period of inhalation or exhalation.

When the breathing is consciously synchronized to these musical cues, the heart rate variability cycle will synchronize with the breathing cycle and remain synchronized as long as the breathing cycle remains aligned with the musical cues. In this way, the human subject can remain in the desired state of coherence of heart rate variability for extended periods of time. Ultimately, this builds familiarity with the desired psycho-physiological condition such that synchronization with the external reference occurs subliminally and with continued practice, the state can be realized at will with or without the external timing reference signal.

For purposes of the present invention, we can consider the cycles of heart rate variability, the periodicity of increasing and decreasing of heartbeat rate, and the breathing cycle, the periodicity of inhalation and exhalation, to be two independent cycles. The relative synchronization of these cycles can vary between 0 and 180 degrees. When these cycles are completely out of phase, heart rate variability is maximally incoherent, when these cycles are completely in phase heart rate variability is maximally coherent.

The fundamental challenge of integrating a 5.88 second interval into music is that the present state of the art standard for musical interval does not accommodate a 5.88 second periodicity. Musical interval is a function of tempo. Tempo according to the present state of the art is defined in terms of beats per minute. This standard was instantiated at the time of Johan Maelzel's improvement on the basic metronome circa 1816. It is Maelzel's Metronome that is the lasting standard for musical tempo today. Consequently, the most basic embodiment of the present invention is the redefinition of musical tempo to incorporate the fundamental 5.88 second interval. A second embodiment of the present invention is the incorporation of this fundamental interval in to the metronome. A third embodiment of the present invention is the incorporation of the fundamental 5.88 second interval into the musical synthesizer for purposes of producing both a reference tempo and music in accordance with the reference tempo.

BRIEF DESCRIPTION OF THE DRAWING FIGURES

The accompanying drawing figures incorporated in and forming a part of this specification illustrate several aspects of the invention, and together with the description serve to explain the principles of the invention.

FIG. 1 presents a table comparing musical tempo according to the present state of the art with the new musical tempo according to the preferred embodiment of the present invention.

DETAILED DESCRIPTION OF THE PREFERRED EMBODIMENTS

The present invention provides a method and system by which a 5.88 second interval may be incorporated into musical composition for the purposes of providing listeners and singers with musical breathing cues with which the breathing cycle is to be consciously synchronized for purposes of synchronizing the heart rate variability cycle with the breathing cycle.

A primary embodiment of the present invention is a standard for tempo that accommodates the fundamental interval of 5.88 seconds. With this tempo standard, musical composition can be created that incorporates recurring melodic sequences for purposes of synchronization of the breathing cycle and listening enjoyment FIG. 1 presents a table comparing tempo according to the present state of the art with tempo according to the preferred embodiment of the present invention. The left section of FIG. 1 100 presents musical tempo according to the present state of the art in beats per minute as defined by Maelzel's Metronome. For purposes of comparison, column 102 presents beats per 60 seconds from 1 beat in 60 seconds to 214 beats in 60 seconds. It is important to note that Maelzel's Metronome addresses the range 40 beats per minute 105 to 208 beats per minute 106. Columns 103 and 104 present corresponding interval in seconds and beats per second, respectively. The right section of FIG. 1 107, presents musical tempo as defined by the preferred embodiment of the present invention incorporating the fundamental 5.88 second interval. As in the left aspect of FIG. 1 100, columns 108, 109, and 110 present beats per 60 seconds, interval in seconds, and beats per second, respectively. Column 111 divides the fundamental 5.88 second period by the interval 109 in seconds.

For tempo to accommodate the 5.88 second period the interval 109 must be evenly divisible into 5.88 seconds. These tempos 112, 113, 114,-132, are identified at every point where they occur between the range of 1 beat in 60 seconds to 214 beats in 60 seconds. The preferred embodiment of the present invention requires the specification of 17 new tempos 112, 113, 114, 115, 117, 118, 119, 120, 122, 123, 124, 125, 127, 128, 129, 130, 132, and the identification of 4 existing tempos 116, 121, 126, and 131 that are evenly divisible into 5.88 seconds, the latter 4 already existing in the present state of the art scheme but heretofore unidentified in terms of their relevance to heart rate variability synchronization. These tempos having been specified per the present invention, musical composition deliberately employing these tempos for purposes of breathing cycle synchronization leading to heart rate variability synchronization may now occur.

Figure 2:
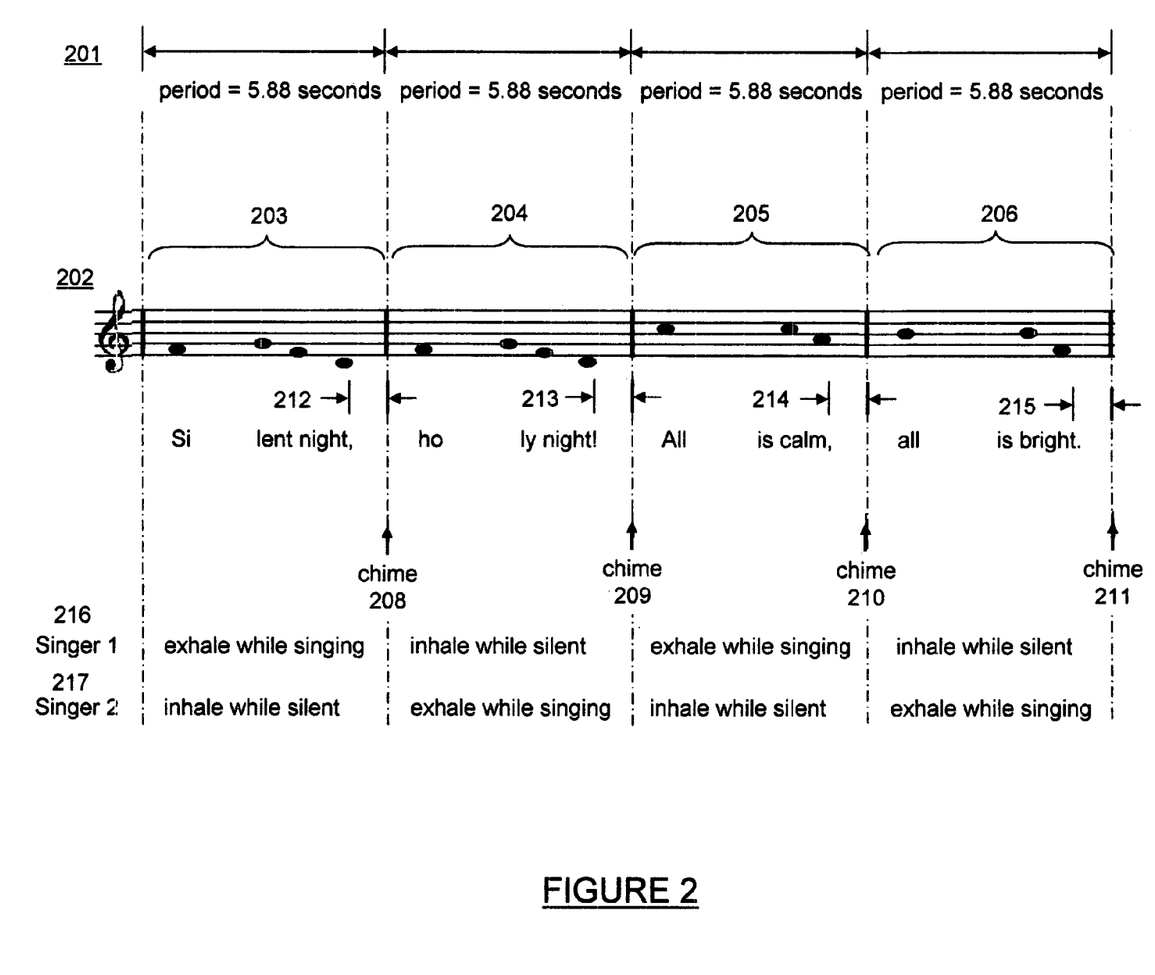
FIG. 2 presents an example of musical composition wherein the present invention is applied.

For purposes of example, FIG. 2 presents an existing musical composition, Silent Night, wherein the present invention is applied. 201 depicts the basic 5.88 second interval occurring sequentially in time. 202 demonstrates the musical staff with 4 bars designated 203, 204, 205, 206, delineating the 5.88 second interval. Bars are delineated by chime 208, 209, 210, 211, the chime signaling the exact moment when the breathing cycle is to change phase from inhalation to exhalation or from exhalation to inhalation. The chime is used only as an example of this musical signal. Similarly, the end of the bar may be signaled with any identifiable musical event including a drum beat, a bass note, etc. Within each bar, a melodic segment occurs. In the case of song, the words of the song are timed such that inhalation and exhalation occur naturally within the bar. For example, in the beginning stanza, Si-lent night, "night" ends slightly before the end of the bar to allow a singer to pause for a moment between the end of "night" and the beginning of inhalation occurring at the end of the bar. This timing is indicated by 212, 213, 214, and 215. This musical method lends itself to different singers 216, 217 singing alternating stanzas such that singer 1 216 is singing while singer 2 217 inhales. Singer 2 217 sings as signer 1 216 inhales and so forth. It should be clear that Silent Night is used merely for purposes of providing an example of a broad method that is generally applicable to all music and vocal accompaniment.

Figure 3:
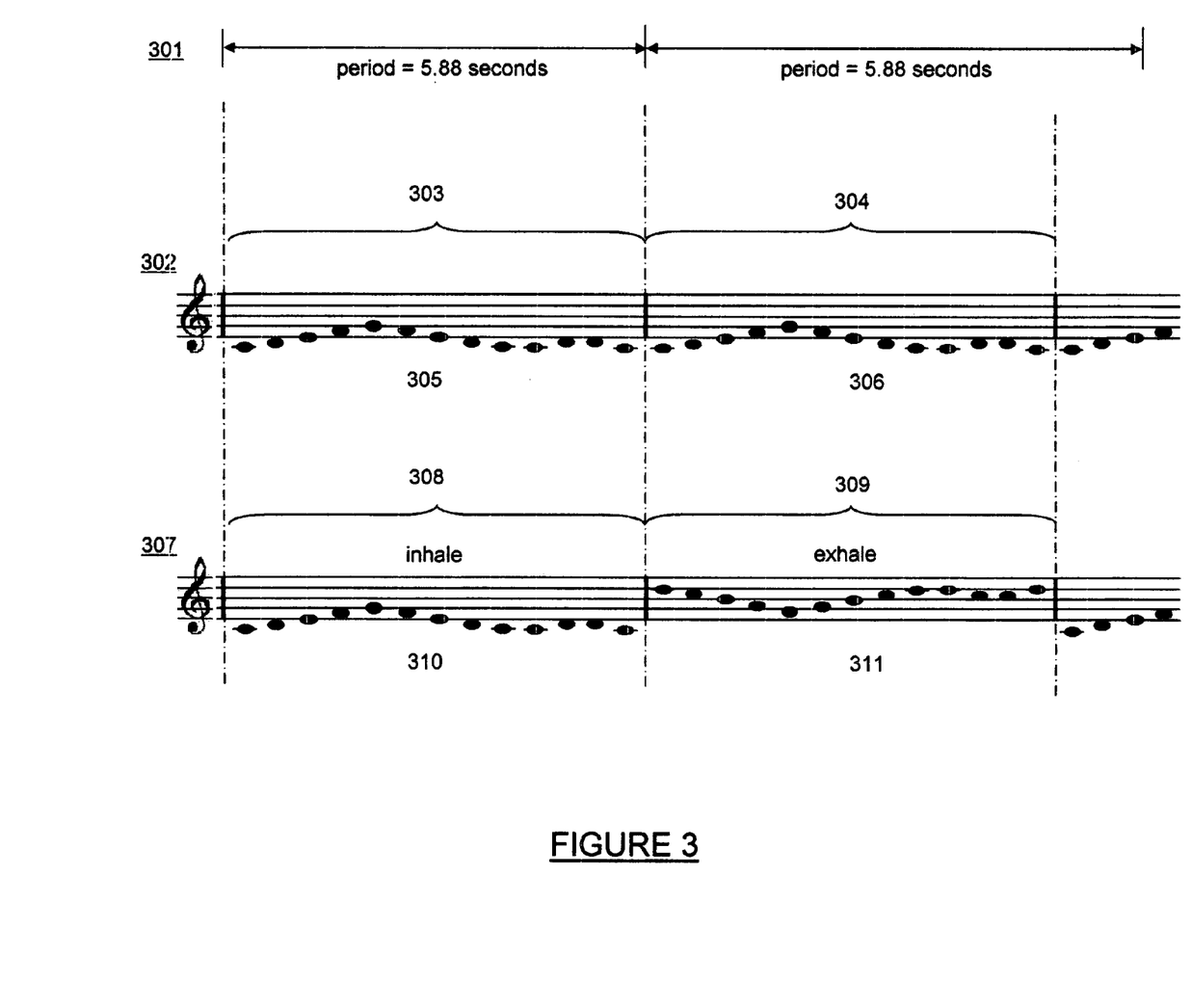
FIG. 3 presents a second example of musical composition wherein the present invention is applied.

Yet another example of the preferred embodiment of the present invention is depicted in FIG. 3, 302 wherein a recurring melodic sequence 305, 306 is played within each 5.88 second bar 303, 304. In this example, a singer or listener changes their breathing phase in between the end of one melodic sequence and the beginning of the next. This continues on a recurring basis throughout the length of the composition. This melodic sequence may occur in either the background, such as a bass, or it may occur in the foreground as the lead harmony. This does not matter as long as the recurring sequence is easily discernable to the human ear such that the singer(s) or listener(s) may consciously synchronize their breathing with it. A second example is identified by 307 wherein melodic sequences signaling inhalation 308 are and exhalation 309 are distinctive.

Figure 4:
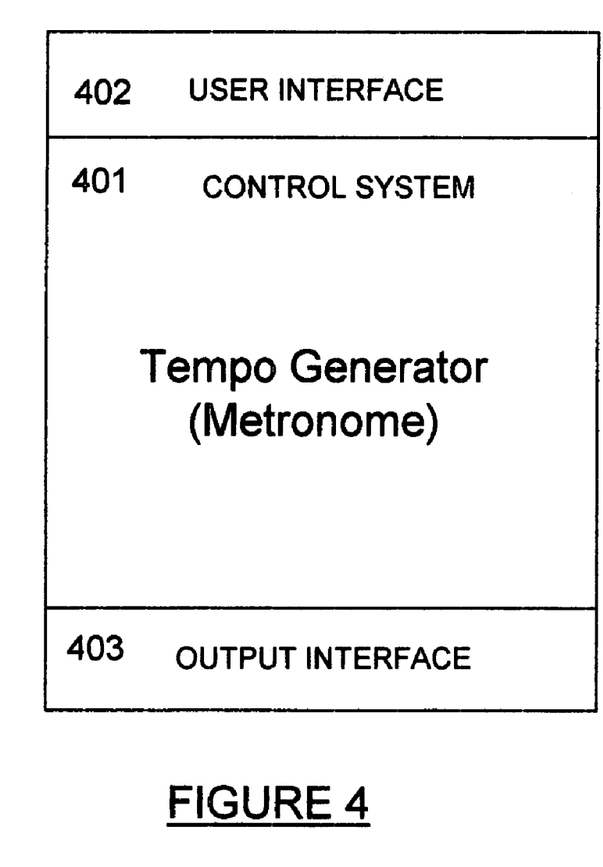
FIG. 4 presents a logical metronome topology.
Figure 5:
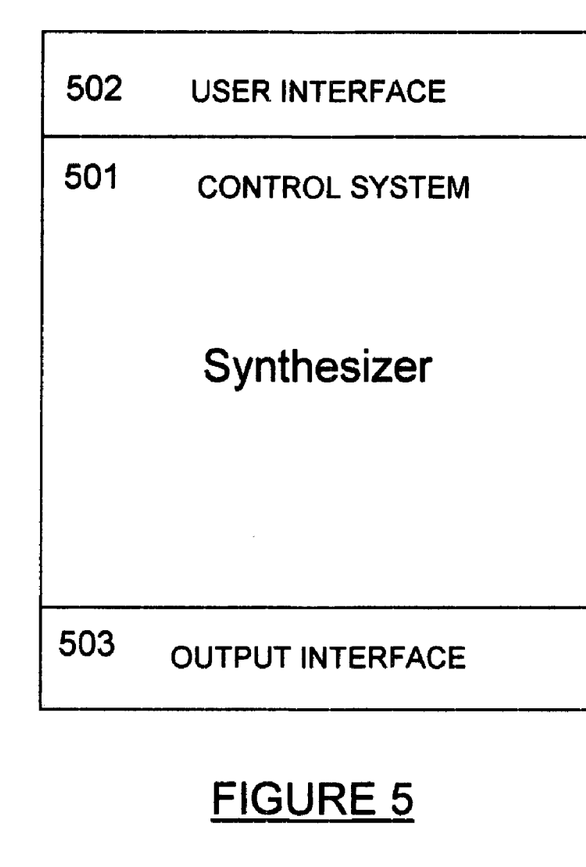
FIG. 5 presents a logical synthesizer topology.

A second fundamental embodiment of the present invention is a tempo generator or metronome capable of supporting the fundamental 5.88 second interval. The tempo generating function may be provided either in the form of a discrete metronome FIG. 4, that is, a functional element exclusively designed to generate tempo to which musical instruments are played in time, or it may be an integral part of a synthesizer FIG. 5 in which case it not only generates the tempo for purposes of musical timing but also produces an audio output that is an integral part of the music being played and potentially recorded. In either case, the tempo generator must be capable of generating timings that are in keeping with the 5.88 second interval. These timings were discussed relative to FIG. 1 will now be presented more exactingly. Either a metronome, or a synthesizer must be capable of generating these specific beats expressed in terms of beats per minute: 10.2 112, 20.4 113, 30.6 114, 40.8 115, 51.0 116, 61.2 117, 71.4 118, 81.6 119, 91.8 120, 102.0 121, 112.2 122, 122.4 123, 132.6 124, 142.8 125, 153.0 126, 163.2 127, 173.4 128, 183.6 129, 193.8 130, 204.0 131, and 214.2 132. Again, it should be noted that this preferred embodiment of the present invention both spans the range of Maelzel's Metronome and also extends the range of beats of interest beyond that of Maelzel's Metronome by providing a lowest order beat of 10.2 beats per minute 112 and a highest order beat of 214.2 beats per minute 132.

Figure 6:
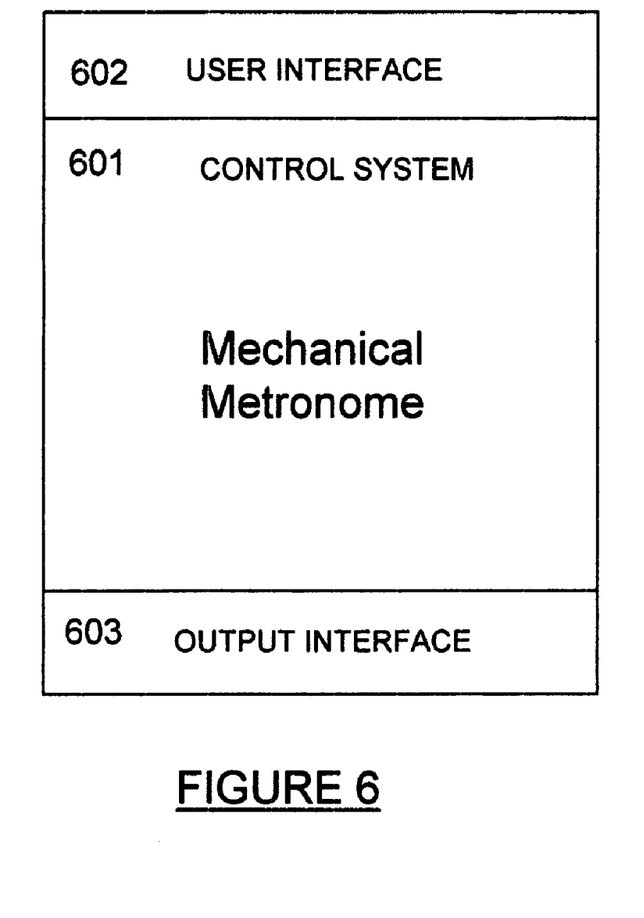
FIG. 6 presents a logical mechanical metronome topology.
Figure 7:
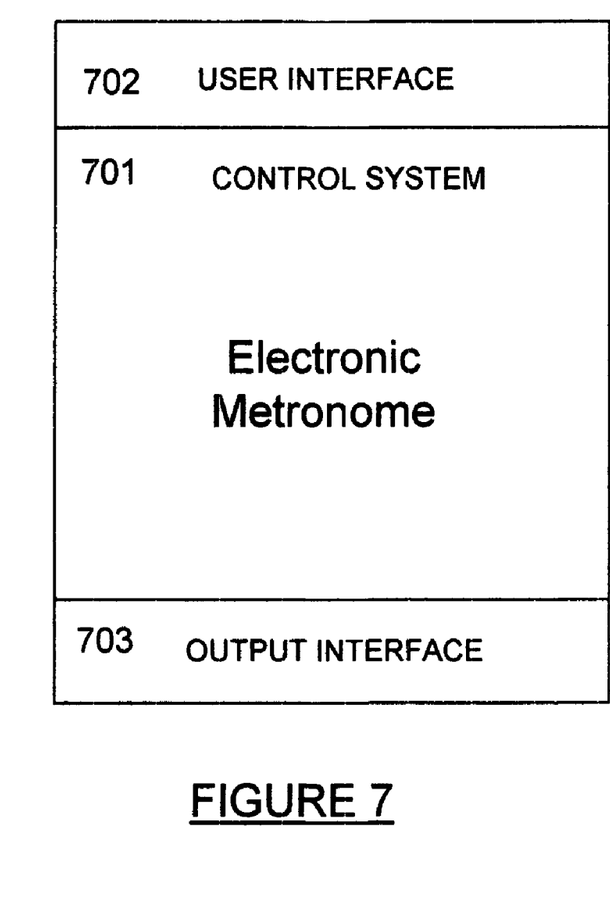
FIG. 7 presents a logical electronic metronome topology.

Referring to FIGS. 6 and 7, metronomes of both the mechanical and electronic variety are intended within the scope of the present invention. The mechanical instance of which is seen as an improvement to Maelzel's Metronome in which the mechanical programmability of specific tempos 112-132 is provided. These tempos may be provided in addition to present tempos or separately. This is to say that an instance of a mechanical metronome may be provided that provides only the tempos according the preferred embodiment of the present invention. The same is true of electronic metronomes, the programmability of which is provided electronically. Both forms of metronome provide some form of control system 601, 701, be it mechanical or electronic, some form of user interface 602, 702, be it mechanical or electronic, and some form of output interface 603, 703, be it mechanical or electronic. Control, user interface, and output interface aspects as they relate to the production of the tempos according to the preferred embodiment of the present invention are assumed within the scope of the present disclosure and accompanying claims.

Figure 8:
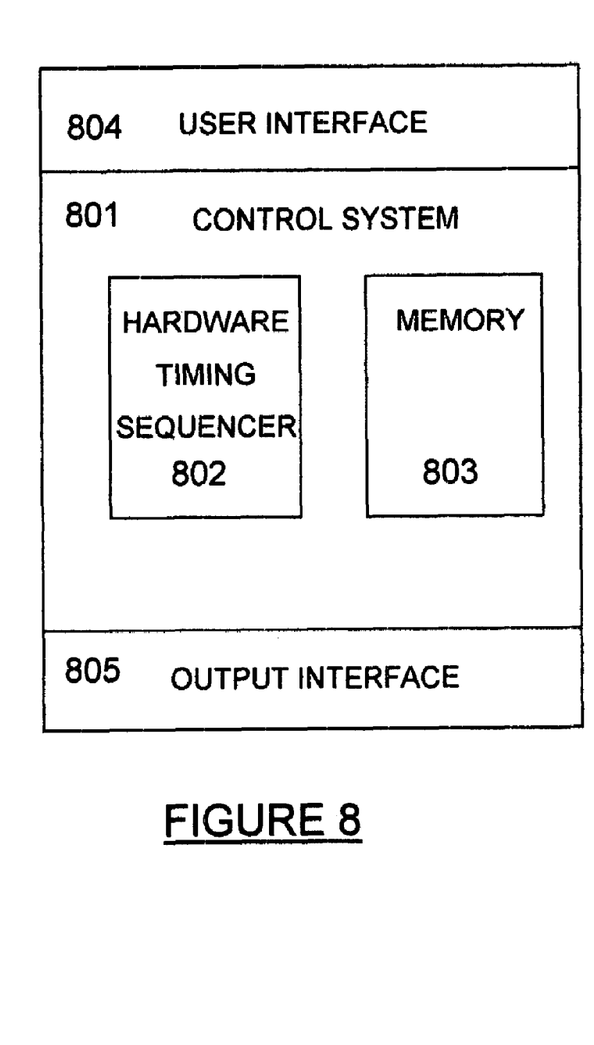
FIG. 8 presents a logical electronic hardware-optimized metronome or synthesizer.
Figure 9:
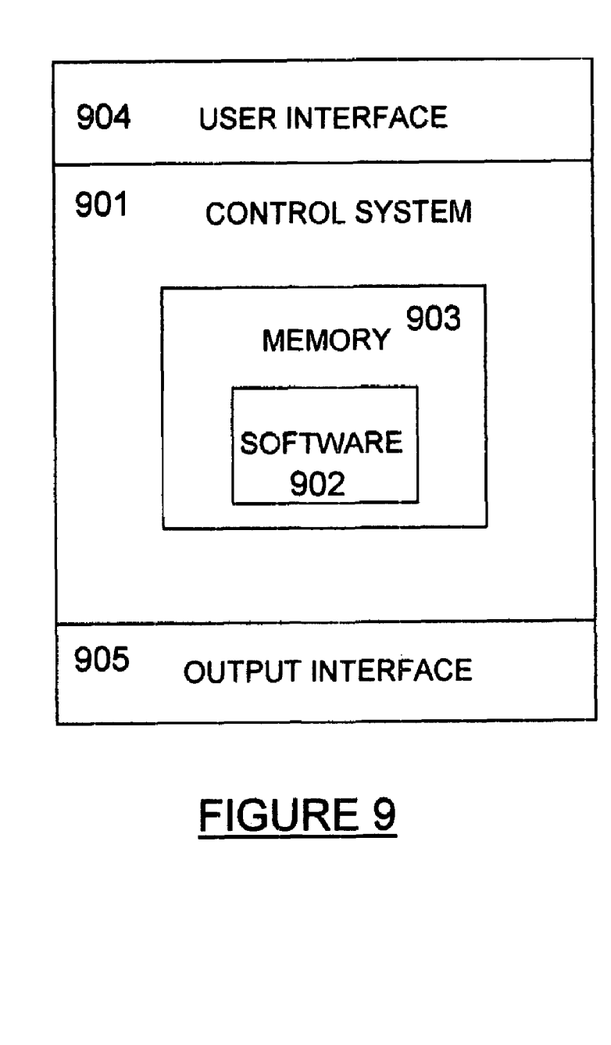
FIG. 9 presents a logical electronic software-optimized metronome or synthesizer.

Referring now to FIGS. 8 and 9, both hardware-optimized and software-optimized topologies of electronic metronomes and synthesizers are assumed within the scope of the present invention. FIG. 8 presents the basic topology and partitioning of a hardware-optimized metronome or synthesizer consisting of a control system 801 comprising hardware timing and sequencer 802 and memory 803, a user interface 804, and an output interface 805. This topology assumes that tempos and related audio signals are generated on the basis of hardware timing and sequencer 802 which may take the form of an integrated circuit, a programmable logic array, or other hardware instantiation. Audio samples or the mathematical equivalent thereof may be stored in memory 803 and accessed according to a hardware oriented timing and sequencing algorithm as determined by the program selection via user interface 804. The resultant audio signal in either analog or digital form and consisting of a tempo of the desired beat and musical characteristics is output via output interface 805. FIG. 9 presents a processor based metronome or synthesizer topology. It consists principally of a control system 901 consisting of a microprocessor, memory, and software. Software programs residing in memory 902 and under the control of the user interface 904, when executed by the microprocessor, generate the analog or digital audio signal which is output via output interface 905. The major classes of electronic metronomes and synthesizers are hardware-optimized and software optimized varieties. It is understood that variations may exist wherein both hardware-optimized and software-optimized methods are employed individually or in combination to varying degree. Those skilled in the art will understand the concepts of the present invention and will recognize applications of these concepts not particularly addressed herein. It should be understood that these concepts and applications fall within the scope of the disclosure and the accompanying claims.

An instructive method is also specified for use with the present invention.

INSTRUCTIVE METHOD

1. Listening participants are instructed to assume a comfortable posture.
2. Listening participants are instructed to relax and listen to the music to identify the 5.88 second interval.
3. The 5.88 second interval is demonstrated to the listening audience such that they are able to identify it and discern it as the music is being played.
4. Individual participants are instructed to inhale and exhale on alternating 5.88 second intervals.
5. Participating groups are instructed to inhale and exhale in such a way as to synchronize their inhalation on certain 5.88 second intervals and synchronization their exhalation on alternating 5.88 second intervals.
6. Listening participants are instructed to continue inhaling and exhaling on alternating 5.88 second intervals for the duration of the music.
7. Singing participants are instructed to sing on alternating 5.88 second intervals such that they are able to sing during one interval and inhale on the next interval.
8. Where there is a song that must be song with continuity, multiple singers are instructed to sing on alternating stanzas such that as the first singer(s) sings the second singer(s) inhales and as the second singer(s) sings the first singer in hales.

What is claimed:

1. A method for composition and creation of music, comprising:
   defining a musical tempo based on a heart rate variability cycle of a human, wherein a fundamental interval of the musical tempo is approximately half of a period of the heart rate variability cycle and the musical tempo includes a plurality of secondary intervals defined by division of the fundamental interval;
   creating a musical composition based upon the defined musical tempo; and
   providing musical breathing cues within the musical composition based on the fundamental interval and the plurality of secondary intervals for the purpose of synchronizing the heart rate variability cycle with a breathing cycle.

2. The method of claim 1 wherein the fundamental interval further comprises 5.88 second interval.

3. The method of claim 2 further comprising defining a primary set of intervals to include 21 intervals.

4. The method of claim 1 further comprising defining a primary set of intervals within the plurality of secondary intervals, wherein intervals within the primary set of intervals are each evenly divisible into 5.88 seconds.

5. The method of claim 1 wherein creating the musical composition based upon the defined musical tempo further comprises repeating the musical breathing cues at a period of at least one of 51 beats per minute, 102 beats per minute, 153 beats per minute, and 204 beats per minute, each being evenly divisible into 5.88 seconds as a multiple of 5 to create an identifiable 5.88 second interval within the musical composition.

6. The method of claim 1 wherein the fundamental interval includes a 5.88 second interval, and further comprising providing the musical breathing cues at the end of each 5.88 second interval to signal a change of phase in the breathing cycle.

7. The method of claim 1 wherein the fundamental interval further comprises a 5.88 second interval and creating a musical composition based upon the defined musical tempo further comprises creating a melodic sequence within the 5.88 second interval such that an end of the melodic sequence indicates a change of phase in the breathing cycle.

8. The method of claim 7 wherein providing the musical breathing cues further comprises providing the melodic sequence to a plurality of singers, wherein the plurality of singers can sing along with the melodic sequence and recognize that the end of the melodic sequence indicates the change of phase in the breathing cycle.

9. The method of claim 8 further comprising instructing the plurality of singers to alternate singing along with the melodic sequence within different measures of the 5.88 second interval, such that as a first one of the plurality of singers sings a second one of the plurality of singers inhales and the first one of the plurality of singers and the second one of the plurality of singers take turns singing.

10. The method of claim 1 further comprising incorporating 21 tempos based on a 5.88 second interval into Maelzel's Metronome.

11. The method of claim 1 further comprising recomposing existing musical compositions to accommodate the fundamental interval, wherein the fundamental interval further comprises a 5.88 second interval.

12. The method of claim 1 further comprising recording and reproducing the musical composition in at least one recorded medium, wherein the fundamental interval further comprises a 5.88 second interval.

13. The method of claim 1 wherein the musical composition includes a 5.88 second interval and further comprising playing the musical composition for live audiences.

14. The method of claim 1 wherein the musical composition includes a 5.88 second interval and further comprising transmitting the musical composition over at least one of a television medium, a radio medium, and an internet medium.

15. The method of claim 1 further comprising defining the plurality of secondary intervals to include 21 intervals with each of the 21 intervals being evenly divisible into 5.88 seconds, incorporating the musical tempo into a metronome, and providing at least one of 51 beats per minute, 102 beats per minute, 153 beats per minute, and 204 beats per minute, wherein the metronome includes at least one of a mechanical metronome and an electronic metronome.

16. The method of claim 1 further comprising defining the plurality of secondary intervals to include 21 intervals with each of the 21 intervals being evenly divisible into 5.88 seconds, incorporating the musical tempo into an electronic synthesizer, and providing at least one of 51 beats per minute, 102 beats per minute, 153 beats per minute, and 204 beats per minute via the electronic synthesizer.

17. The method of claim 1 wherein the fundamental interval includes a 5.88 second interval, and further comprising performing the musical composition as part of at least one of a live and a recorded performance.

18. The method of claim 1 wherein the fundamental interval includes a 5.88 second interval, and further comprising instructing a singer to alternate singing and inhaling on alternating instances of the 5.88 second interval.

19. The method of claim 1 wherein the fundamental interval includes a 5.88 second interval, and further comprising instructing a plurality of singers to sing stanzas on alternating instances of the 5.88 second interval such that as a first one of the plurality of singers sings a second one of the plurality of singers inhales and the first one of the plurality of singers and the second one of the plurality of singers take turns singing.

20. The method of claim 1 wherein the fundamental interval includes a 5.88 second interval, and further comprising differentiating the musical breathing cues to identify a beginning and an end of the 5.88 second interval and differentiating between alternating instances of the 5.88 second interval for inhalation and exhalation.

21. A system for composition and creation of music, comprising:
a tempo generator adapted to define a musical tempo based on a heart rate variability cycle of a human, wherein a fundamental interval of the musical tempo is approximately half of a period of the heart rate variability cycle and the musical tempo includes a plurality of secondary intervals defined by division of the fundamental interval; and
a control system adapted to:
create a musical composition based upon the defined musical tempo; and
provide musical breathing cues via the tempo generator within the musical composition based on the fundamental interval and the plurality of secondary intervals for the purpose of synchronizing the heart rate variability cycle with a breathing cycle.

22. The system of claim 21 wherein the tempo generator further comprises at least one of a metronome and a synthesizer.

23. The system of claim 22 wherein the metronome further comprises at least one of a mechanical metronome and an electronic metronome.

24. The system of claim 21 wherein the tempo generator is further adapted to define the fundamental interval to include a 5.88 second interval.

25. The system of claim 21 wherein the tempo generator is further adapted to define a primary set of intervals within the plurality of secondary intervals, wherein intervals within the primary set of intervals are each evenly divisible into 5.88 seconds.

26. The system of claim 21 wherein the tempo generator is further adapted to define a primary set of intervals to include 21 intervals.

27. The system of claim 21 wherein the control system is further adapted to repeat the musical breathing cues at a period of at least one of 51 beats per minute, 102 beats per minute, 153 beats per minute, and 204 beats per minute, each being evenly divisible into 5.88 seconds as a multiple of 5 to create an identifiable 5.88 second interval.

28. The system of claim 21 wherein the control system is further adapted to repeat the musical breathing cues at a period other than 51 beats per minute, 102 beats per minute, 153 beats per minute, and 204 beats per minute.

29. The system of claim 21 wherein the fundamental interval further comprises a 5.88 second interval, and the control system is further adapted to provide the musical breathing cues at the end of each 5.88 second interval to signal a change of phase in the breathing cycle.

30. The system of claim 21 wherein the fundamental interval further comprises a 5.88 second interval and the control system is further adapted to create a melodic sequence within the 5.88 second interval such that an end of the melodic sequence indicates a change of phase in the breathing cycle.

31. The system of claim 30 wherein the control system is further adapted to provide the melodic sequence to a plurality of singers, wherein the plurality of singers can sing along with the melodic sequence and recognize that the end of the melodic sequence indicates the change of phase in the breathing cycle.

32. The system of claim 31 wherein the control system is further adapted to instruct the plurality of singers to alternate singing along with the melodic sequence within different measures of the 5.88 second interval, such that as a first one of the plurality of singers sings a second one of the plurality of singers inhales and the first one of the plurality of singers and the second one of the plurality of singers take turns singing.

33. The system of claim 21 wherein the control system is further adapted to incorporate 21 tempos based on a 5.88 second interval into Maelzel's Metronome.

34. The system of claim 21 wherein the control system is further adapted to recompose existing musical compositions to accommodate the fundamental interval, wherein the fundamental interval further comprises a 5.88 second interval.

35. The system of claim 21 wherein the tempo generator is further adapted to define the plurality of secondary intervals to include 21 intervals with each of the 21 intervals being evenly divisible into 5.88 seconds, and wherein the control system is further adapted to provide outputs of the 21 intervals in at least one of an analog format and a digital format.

36. The system of claim 21 wherein the control system is further adapted to record and reproduce the musical composition in at least one recorded medium, wherein the fundamental interval further comprises a 5.88 second interval.

37. The system of claim 21 wherein the control system is further adapted to create the musical composition to include a 5.88 second interval and to play the musical composition for live audiences.

38. The system of claim 21 wherein the control system is further adapted to create the musical composition to include a 5.88 second interval and to transmit the musical composition over at least one of a television medium, a radio medium, and an internet medium.

39. The system of claim 21 wherein the tempo generator is further adapted to define the plurality of secondary intervals to include 21 intervals with each of the 21 intervals being evenly divisible into 5.88 seconds, and to provide at least one of 51 beats per minute, 102 beats per minute, 153 beats per minute, and 204 beats per minute.

40. The system of claim 21 wherein the tempo generator is further adapted to define the fundamental interval to include a 5.88 second interval, and the control system is further adapted to perform the musical composition as part of at least one of a live and a recorded performance.

41. The system of claim 21 wherein the tempo generator is further adapted to define the fundamental interval to include a 5.88 second interval, and the control system is further adapted to instruct a singer to alternate singing and inhaling on alternating instances of the 5.88 second interval.

42. The system of claim 21 wherein the tempo generator is further adapted to define the fundamental interval to include a 5.88 second interval, and the control system is further adapted to instruct a plurality of singers to sing stanzas on alternating instances of the 5.88 second interval such that as a first one of the plurality of singers sings a second one of the plurality of singers inhales and the first one of the plurality of singers and the second one of the plurality of singers take turns singing.

43. The system of claim 21 wherein the tempo generator is further adapted to define the fundamental interval to include a 5.88 second interval, and the control system is further adapted to differentiate the musical breathing cues to identify a beginning and an end of the 5.88 second interval and to differentiate between alternating instances of the 5.88 second interval for inhalation and exhalation.

* * * * *